United States Patent [19]  [11] 4,416,735
Kissel  [45] Nov. 22, 1983

[54] DILUENT AND METHOD FOR POTENTIOMETRIC ASSAY OF LIQUIDS

[75] Inventor: Thomas R. Kissel, Rochester, N.Y.

[73] Assignee: Eastman Kodak Company, Rochester, N.Y.

[21] Appl. No.: 389,515

[22] Filed: Jun. 17, 1982

[51] Int. Cl.$^3$ .................. G01N 27/46; G01N 1/00
[52] U.S. Cl. .................. 204/1 T; 252/408.1; 260/501.17; 436/74; 436/79; 436/174; 436/179; 564/503
[58] Field of Search .................. 436/74, 79, 108, 150, 436/174, 175, 176, 179, 16; 204/1 A, 1 T; 564/503; 252/408.1; 260/501.17

[56] References Cited

U.S. PATENT DOCUMENTS

| | | | |
|---|---|---|---|
| 2,200,184 | 5/1940 | Morgan | 564/503 X |
| 3,250,676 | 5/1966 | Stachel et al. | 167/51.5 |
| 3,938,954 | 2/1976 | Stavropoulos et al. | 436/74 |
| 4,053,381 | 10/1977 | Hamblen et al. | 204/195 M |
| 4,214,968 | 7/1980 | Battaglia et al. | 204/195 M |
| 4,324,685 | 4/1982 | Louderback | 252/408 |

FOREIGN PATENT DOCUMENTS 1305644 2/1973 United Kingdom.

OTHER PUBLICATIONS

Joseph S. Annino, Clin. Chem., 13, 227, 1967.
H. Jacobsen, Anal. Chem., 36, 13, pp. 1951–1954, (1966).
Instruction Manual Nova 1, Nova Biomedical, (1978).
Jack H. Ladenson, Clin. Chem., 25, 5, 757, (1979).

*Primary Examiner*—G. L. Kaplan
*Attorney, Agent, or Firm*—Dana M. Schmidt

[57] ABSTRACT

A diluent and a method of assaying are described, by which the ionic strength range of the liquid that is to be assayed potentiometrically, is compressed. The diluent comprises a predetermined concentration of (a) a protonated water-soluble organic amine having (i) a pKa greater than or equal to 9.3, and (ii) a hydroxyalkyl of 1 to 5 carbon atoms, bonded to the nitrogen of the amine, wherein the oxygen-to-carbon bond of the hydroxy is no more than two bonds removed from the nitrogen, and (b) an acid anion.

14 Claims, No Drawings

DILUENT AND METHOD FOR POTENTIOMETRIC ASSAY OF LIQUIDS

FIELD OF THE INVENTION

This invention relates to a diluent that is added to a liquid to be assayed, and a method for potentiometrically determining ionic concentration, by which the ionic strength range of the liquid is compressed to a useful range.

BACKGROUND OF THE INVENTION

In assaying urine samples for electrolytes, a common problem that complicates the assay is the wide range of ionic strengths that potentially occur in the samples. That is, the ionic strength can range from about 50 to about 400 millimolar, depending on the health of the patient. Such a 10 to 1 range tends to create errors because of the variation in activity coefficients and junction potentials that occur over that range.

Therefore, it is common practice to add a charged diluent to the urine to compress the ionic range. For example, if 4 parts of a diluent of 150 millimolar strength are added to 1 part of urine, the above-noted range of 50 to 400 is compressed as follows: Only 1/5 of the mixture is urine, so the urine's ion strength will be from 10 to 80 millimolar. Adding the 150 millimolar of the diluent produces a range of 160 to 230 millimolar, a much more acceptable and workable range.

A further common problem, particularly in certain biological liquids such as urine, has been the presence of $NH_4\oplus$, either because of pathologies of the patient or because of sample aging. The ammonium cation is a known interferent for a number of assays. To avoid this problem, it is known to use a diluent having a pKa that is large enough to convert ammonium to ammonia. Thus, if ammonium is a potential interferent, a diluent such as Tris buffer, which has the structural formula $(HO-CH_2)_3C-N\oplus H_3\ Z\ominus$ where Z is an acid anion, is considered to be inferior because the pKa is not greater than or equal to 9.3.

Even if the pKa is sufficiently high, conventional diluents present a further problem. Recent developments have provided an improved method for conducting potentiometric assays of serum using a pair of disposable ion-selective electrodes (hereinafter, "ISE's"). Such ISE's are mounted in a plastic frame and permit rapid processing at high through-put rates in an automated analyzer, for example the analyzer available under the trademark "Kodak EKTACHEM 400" from Eastman Kodak Co. The plastic frame and ISE's are further described in U.S. Pat. No. 4,053,381, issued on Oct. 11, 1977, and U.S. Pat. No. 4,214,968, issued on July 29, 1980. Such ISE's comprise a dried internal reference electrode comprising the residue of a solution of a salt and a hydrophilic polymeric binder in a solution for the polymer and the salt. In contact with the reference electrode, there is a hydrophobic ion-selective membrane comprising a hydrophobic binder and an ion carrier in a carrier solvent. The use of two such ISE's with a patient sample and a reference liquid having a known concentration of the ion in question provides a differential measurement. Because of the ease and speed with which such assays of serum are accomplished, it is desirable that other types of liquids be assayed on such analyzers. The use of the aforedescribed ISE's and analyzer with other liquids besides serum is becoming an accepted practice. However, when assaying liquids such as urine, the presence of a cationic diluent as noted above introduces the potential of an interferent, as follows: Certain ISE's of the aforementioned patent, particularly those used to assay for $Na\oplus$, feature an ionophore that is not always selective enough to preclude detection of certain interferents. As a result, the cations of many conventional diluents tend to act as interferents when testing, e.g., for $Na\oplus$. The interference shows up in the slope of the calibration curve (millivolts versus the log of the analyte concentration) in that the slope is reduced compared to the Nernstian ideal (60 millivolts/decade). Reductions in slope are caused by a departure from linearity in the calibration curve, primarily at the low ion concentrations. If the slope is reduced to 55 or less, the error at low ion concentrations is so large that the assay is unacceptable. Thus, for example, the diluent described in *Anal. Chem.*, Vol. 38, pp. 1951-1954 (1966), namely diethylamine, acetate salt, produces a slope of less than 55 when used to assay liquids using the above-noted ISE's.

Therefore, prior to this invention there has existed a need for a charged diluent, useful for example in assaying urine electrolytes, that does not act as an interferent for $Na\oplus$ when using an ISE especially of the type described in the aforesaid U.S. patents, while at the same time reducing the ammonium interference.

SUMMARY OF THE INVENTION

I have discovered that certain water-soluble organic amines are useful in diluents for aqueous samples having a large ionic strength range, in that they result in no significant interference when the aforedescribed ISE's are used for the assay of electrolyes in aqueous samples.

Thus, there is advantageously featured a protonated amine-containing diluent for liquids such as urine, which though containing a cation, does not act as an interferent when assaying for $Na\oplus$ using the ISE's described in U.S. Pat. Nos. 4,053,381 and 4,214,968.

A further advantageous feature is that, the protonated amine of the diluent acts to prevent interference from ammonium ions.

These advantageous features arise from a diluent which comprises an aqueous solution having a pH of at least about 10.0 and a predetermined concentration of (a) a protonated water-soluble organic amine having (i) a pKa greater than or equal to about 9.3, and (ii) a hydroxyalkyl of 1 to 5 carbon atoms, bonded to the nitrogen of the amine, wherein the oxygen-to-carbon bond of the hydroxy is no more than two bonds removed from the nitrogen and (b) an acid anion.

Such a diluent is particularly useful when admixed with urine.

The diluent provides a method for potentiometrically determining the concentration of an ionic analyte in an aqueous solution over a relatively narrow range. The steps of the method comprise (i) admixing with the aqueous solution, a predetermined concentration of the protonated amine noted above, and the accompanying acid anion;

(ii) contacting a quantity of the admixture with a first electrode selective for the ionic analyte;

(iii) before, during, or after step (ii), contacting a quantity of a reference liquid having a known concentration of the analyte, with a second electrode; and (iv) allowing the quantities of liquids to make ion contact with each other to permit a detection of electrical imbalance between them.

Other features and advantages will become apparent upon reference to the following Description of the Preferred Embodiments.

DESCRIPTION OF THE PREFERRED EMBODIMENTS

The preferred embodiments are herein described in connection with potentiometric assays of $Na^{\oplus}$ in urine using the ISE's described in U.S. Pat. Nos. 4,053,381 or 4,214,968. (The details of those patents concerning the ISE's and the frames supporting them are expressly incorporated herein by reference.) In addition, the diluents of this invention are useful when potentiometrically assaying for other ions, such as $K^{\oplus}$, using the above as well as other kinds of electrodes, particularly those electrodes that are sensitive to interference from cations. Furthermore, these diluents are useful when assaying other ion-bearing biological and industrial liquids, for example, sweat and waste water.

The instant invention concerns a diluent that compresses the ionic strength range of an ion-bearing liquid under test. For this reason, the diluent comprises primarily a protonated compound, which according to the invention is an organic amine salt. The amine is water-soluble so that the diluent is useful with aqueous liquids such as urine.

More specifically, I have discovered that a class of protonated, water-soluble organic amine alcohols are particularly useful in a diluent to produce no significant interference, wherein the amines have a pKa equal to or greater than 9.3 and most preferably, at least 9.8, and the substituents bonded to the nitrogen of the amine are as described in the Summary. Any such amine is useful. As used herein, "significantly noninterfering" or "no significant interference" means, the interference, if any, does not cause the calibration curve, when prepared, to have an overall slope outside the range of between about 55 and 65 millivolts/decade, a range that is consistent with the Nernstian slope of 60 mV/decade.

Particularly preferred are amine salts having the structural formula

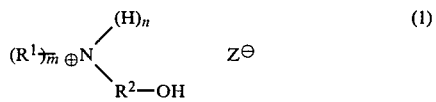  (1)

wherein $R^1$ is alkyl of 1 to 5 carbon atoms, such as methyl, ethyl, propyl, i-propyl, butyl, t-butyl and the like; $R^2$ is alkylene preferably containing from 1 to 5 carbon atoms such as methylene, ethylene, propylene, i-propylene, butylene, and the like, the oxygen-to-carbon bond of the hydroxy being no more than 2 bonds removed from the nitrogen; m is 0, 1 or 2; n is (3-m); and Z is an acid anion, for example, acetate, chloride, nitrate, and the like. The cationic charge and the acid anion are obtained by neutralizing the amine in the appropriate acid until the desired pH of the solution is reached. Preferably, the pH is no less than 10.0, and most preferably, about 10.3.

Useful salts of the diluent include those listed in Table I:

Table I 2-(diethylamino)-1-ethyl alcohol, acetate salt;
2-amino-1-ethyl alcohol, acetate salt;
2-ethylamino-1-ethyl alcohol, acetate salt;
2-isopropylamino-1-ethyl alcohol, acetate salt;
1-(diethylamino)-2-propyl alcohol, acetate salt; and
1-(dimethylamino)-2-methyl-1-propyl alcohol, acetate salt.

Of the aforesaid list, particularly preferred are 2-(diethylamino)-1-ethyl alcohol, 2-amino-1-ethyl alcohol, and 2-ethylamino-1-ethyl alcohol. As previously noted, salts similar to any of those described above, except that the acid anion is selected from some other acid, are useful.

Not all amine alcohols falling within the scope of compounds defined by $R^1$ and $R^2$ above are useful, because they are not all water-soluble. For example, 2-(dibutylamino)-1-ethyl alcohol is not water-soluble. If one of $R^1$ is a long chain alkyl of, for example, 5 carbon atoms, the other $R^1$ is selected to be sufficiently less than four carbon atoms in length to provide water solubility.

The above-noted amine alcohols are either readily available as known compounds, or are synthesized by conventional methods known to the art.

Preferably, the diluent includes additional ingredients. To provide the diluent with a particular inherent viscosity, enough water-soluble polymer, such as polyvinylpyrrolidone or polyvinyl alcohol, is added until the solution has a viscosity of between about 1.3 centipoise and about 1.9 centipoise when measured at 25° C. on a viscometer such as that available from Cannon Instrument co. under the trademark "Cannon Manning Semi-micro Viscometer No. 75." To complex $Ca^{\oplus\oplus}$ and $Mg^{\oplus\oplus}$ ions so as to prevent them from precipitating out at the preferred diluent pH of at least 10.0, (ethylenedinitrilo)tetraacetic acid (hereinafter "EDTA") is added.

The predetermined concentration of the salt of the diluent is such that the diluent compresses the ionic range of the aqueous liquid under test, to the desired value. The actual amount of the salt varies, depending upon the liquid being assayed and the range of ions that is to be detectable after dilution. Most preferably, after the diluent is added the range of ionic strength of the test liquid is between about 150 millimolar and about 250 millimolar.

A useful test to determine whether a particular diluent solution has a satisfactory concentration, is as follows: two saline solutions are prepared, one with a total ionic strength of 130 millimolar and the other with a total ionic strength of 410 millimolar (using the relationship total ionic strength I equals ½ the sum of $\Sigma C_i \times Z_i^2$ wherein $C_i$ is the ion concentration and $Z_i$ the charge of the ion). Four parts of the diluent solution are added to 1 part of each of the two solutions, and the two admixtures so formed are checked for total ionic strength. If in the two admixtures, the total ionic strengths are within the range of about 150 millimolar to about 250 millimolar, the concentration of the diluent solution is satisfactory.

In the case of urine, preferably the predetermined concentration of the amine salt is such that the ionic strength I of the diluent is about 150 millimolar. Using 2-(diethylamino)-1-ethyl alcohol (hereinafter "DEAE") protonated with 75-85 millimolar acetic acid, this requires about 0.52 moles of DEAE in a liter of water.

The diluent is then used 4 parts thereof to 1 part of the urine, to compress the urine ionic strength to a range of about 150 millimolar to about 250 millimolar for human patients.

The above-noted range of about 150 millimolar to about 250 millimolar is preferred because the ion activity coefficients for the afore-described ISE's are relatively constant within that range. It will be readily apparent that the same range can be achieved by adding more diluent solution having, e.g., only 0.42 molar concentration, or less diluent solution having a concentration greater than 0.52 molar. However, if the diluent salt is added at concentrations much greater than 0.52 molar, for example, 1.5 molar, it has been found that interference occurs as measured by the slope of the calibration curve. Also, if too much diluent solution (at a low original concentration) is added, the ion of the test liquid under detection may be reduced below the lower detection limit of the ISE.

If the test liquid is other than urine, the amount of diluent to be added to achieve the aforesaid range of about 150 millimolar to about 250 millimolar is readily determined by ascertaining the expected limits of ionic strength for that test liquid, and adding diluent accordingly.

Urine electrolyte assays are preferably conducted using the afore-described ISE's in a differential measurement in which two identical electrodes selective, for example, for $Na^\oplus$, are used side by side with a quantity of the diluted urine sample from the patient in contact with one, and a reference liquid having a known $Na^\oplus$ concentration in contact with the other. More specifically, a useful example of such an ISE is a $Na^\oplus$ clinical chemistry slide comprising, in laminated array, a layer of silver, a layer of silver chloride, a layer of NaCl in a deionized gelatin binder, and a layer of methyl monensin and bis(2-ethylhexyl)sebacate in carboxylated polyvinyl chloride. During the assay, the two quantities of liquid are allowed to come into ionic contact with each other on or in an ion bridge, for example, a paper bridge, and a potentiomter is placed in contact with the electrodes to detect the electrical imbalance created by the different activity of the ionic analyte in the patient sample, compared to the reference liquid. See, for example, the procedure described in the aforesaid U.S. Pat. No. 4,053,381.

The above-described diluent, prepared with water as the solvent, when admixed with the aqueous sample to be tested, produces calibration curves for $Na^\oplus$, using the afore-described ISE's, that maintain a slope of between about 55 and about 65 millivolts/decade of concentration of $Na^\oplus$. Such calibration curves demonstrate conclusively the lack of significant interference that results when using the diluent of this invention to conduct potentiometric assays using the above-described ISE's.

The mechanism by which the interference is reduced by this invention is not completely understood. However, I have found that, surprisingly, significant interference is produced by the diluent if the hydroxyl group is too far removed from the nitrogen, i.e., by attachment to a carbon atom which is more than 2 bonds removed from the nitrogen atom.

EXAMPLES

The following Examples further illustrate the invention.

In each of the examples set forth hereinafter, the electrode of the test were the $Na^\oplus$ clinical chemistry slides described in the aforesaid U.S. Pat. No. 4,214,968, obtained from Eastman Kodak Co. under the trademark "Kodak EKTACHEM".

EXAMPLE 1—Use of DEAE 0.52 moles of DEAE, and 2.92 g of EDTA were added to several hundred mL of deionized water and stirred until dissolved. More water was added to bring the solution to about 800 mL, at which time the pH was adjusted to 10.5 by adding 75–85 mmoles acetic acid. The solution was then diluted by water to 1 liter. 4 parts of this solution were added to 1 part of each of two calibrators which comprised 60 mM and 225 mM NaCl, respectively. Calibration curves were then prepared to check the slope values.

As comparative examples, similar diluents were obtained as above, except that 0.52 molar of the following amines were used in place of DEAE:

TABLE I

| Comparative Examples | Amine |
| --- | --- |
| C.E. 1 | Diethylamine, acetate salt (or "DEA") |
| C.E. 2 | Ethylamine, acetate salt (or "EA") |
| C.E. 3 | Triethylamine, acetate salt (or "TEA") |

In all cases, the prepared diluents had a pH of 10.5.

Table II sets forth the predicted (or Nernstian) slopes as well as the actual observed slopes obtained from the diluted calibrators prepared as noted above. (The reference liquid comprised 2 M KCl and 5.0 g/l of polyvinylpyrrolidone.)

TABLE II

| Example | Amine | Predicted Slope (mV/Decade) | Observed Slope (mV/Decade) |
| --- | --- | --- | --- |
| C.E. 1 | DEA | 59.05 | 30.15 ± 1.0 |
| C.E. 2 | EA | 59.05 | 36.01 ± 0.3 |
| C.E. 3 | TEA | 59.05 | 20.30 ± 0.3 |
| Example 1 | DEAE | 59.05 | 62.44 ± 0.7 |

Thus, of these only DEAE demonstrated no significant interference, that is, a slope that was between about 55 and about 65 mV per decade.

EXAMPLES 2 and 3—Other Diluents

The procedure of Example 1 was repeated, except that 0.52 molar of the amines of Table III, neutralized with acetic acid as in Example 1, were used in the diluent, 8 mM of EDTA was used, and 5 g/l of polyvinylpyrrolidone were added to the diluent in each case. The Comparative Example 4 comprises an amine wherein the OH group is more than two bonds removed from the nitrogen atom.

TABLE III

| Example | Amine | Predicted Slope (mV/decade) | Observed Slope (mV/decade) |
| --- | --- | --- | --- |
| Com. Ex. 4 | 3-(diethylamino)-1-propyl alcohol, acetate salt | 59.1 | 52.8 ± 0.2 |
| 2 | 2-amino-1-ethyl-alcohol, acetate salt | 59.1 | 62.3 ± 0.2 |
| 3 | 2-ethylamino-1-ethyl alcohol | 59.1 | 60.7 ± 0.2 |

The results of C.E. 4 demonstrated the importance in having the oxygen-to-carbon bond of the —OH group no more than two bonds removed from the nitrogen atom. The slope of 52.8 was unacceptable.

EXAMPLES 4–8—Simulated Urine Dilution

To simulate use with urine, the following synthetic solutions of salts were prepared.

TABLE IV

| Test Liquids: Ions* | Amounts of Ion (mM) in Test Liquid Nos. | | | | |
|---|---|---|---|---|---|
| | 1 | 2 | 3 | 4 | 5 |
| Na⊕ | 40 | 70 | 80 | 160 | 250 |
| K⊕ | 100 | 20 | 50 | 60 | 100 |
| Ca ++ | 5 | 1.5 | 5 | 4 | 1.5 |
| Mg ++ | 4 | 1 | 4 | 3.5 | 4 |
| NH4⊕ | 40 | 20 | 100 | 30 | 30 |
| Cl⊖ | 133 | 85 | 161 | 202 | 350 |
| SO4 = | 20 | 10 | 15 | 19 | 15 |
| H2PO4⊖ | 25 | 10 | 50 | 25 | 11 |
| pH | 5.5 | 6.0 | 4.0 | 6.0 | 6.0 |
| I** | 230 | 130 | 280 | 290 | 410 |

*Salts used to obtain these were NH4Cl, NaH2PO4, KCl, NaCl, MgSO4, CaCl2, Na2SO4, K2SO4 and MgCl2 in deionized H2O.
**Total ionic strength, millimolar.

Test liquid No. 2 simulated a low total ionic strength urine, whereas liquid No. 5 simulated a very high total ionic strength urine. These were diluted with DEAE following the procedure of Example 1, and measured for Na⊕ using the ISE's of Example 1. Following the dilution step, the total ionic strength of these solutions ranged from 176 millimolar (No. 2) to 232 millimolar (No. 5), well within the desired range noted above. The reference liquid was 2 M KCl prepared in the DEAE diluent. The results appear in Table V, along with the predicted analyte concentrations, the bias, and the % bias, compared to the predicted values.

TABLE V

| Example | Test Liquid No. | Predicted [Na⊕] mM | Measured [Na⊕] mM | Bias mM | % Bias |
|---|---|---|---|---|---|
| 4 | 1 | 40 | 38.4 ± 1.6 | −1.6 | −4.0 |
| 5 | 2 | 70 | 72.3 ± 0.6 | +2.3 | +3.3 |
| 6 | 3 | 80 | 83.0 ± 1.3 | +3.0 | +3.8 |
| 7 | 4 | 160 | 158.0 ± 1.8 | −1.99 | −1.2 |
| 8 | 5 | 250 | 246.6 ± 3.8 | −3.4 | +3.3 |

Inasmuch as accuracy and precision within ±5% are considered to be acceptable, all of these examples demonstrated satisfactory performance by the diluent. This is particularly noteworthy for examples 5 and 8 which involves test liquid Nos. 2 and 5 having the extreme ionic strength values.

EXAMPLE 9—Test with Urine

The procedure of Example 4 were repeated, using however actual urine samples obtained from 15 different patients in place of the synthetic saline solutions. The Na⊕ concentrations following the procedure of Example 4 were checked against the values obtained from a flame photometer from Corning Medical & Scientific, a division of Corning Glass Works. When plotted as ISE Na⊕ concentrations vs. the flame photometer values, the correlation demonstrated a slope of 1.1±0.02 with an average bias of −2.5% and a standard deviation from the plot ($S_{y.x}$) of 4.04 mM. The DEAE diluent thus demonstrated adequate performance when used to dilute urine for a Na⊕ assay using the above-noted Na⊕ ISE's.

The invention has been described in detail with particular reference to preferred embodiments thereof, but it will be understood that variations and modifications can be effected within the spirit and scope of the invention.

What is claimed is:

1. In admixture, a urine sample selected for potentiometric assay, and a diluent for said sample, said diluent comprising an aqueous solution having a pH of at least about 10.0 and a predetermined concentration of
    (a) a protonated water-soluble organic amine having (i) a pKa greater than or equal to about 9.3, and (ii) a hydroxyalkyl of 1 to 5 carbon atoms, bonded to the nitrogen of the amine, wherein the oxygen-to-carbon bond of the hydroxy is no more than two bonds removed from the nitrogen and
    (b) an acid anion,
    said predetermined concentration being effective to produce a total ionic strength of said admixture within the range of about 150 millimolar and about 250 millimolar.

2. An admixture as defined in claim 1, wherein said amine is selected from the group consisting of 2-(diethylamino)-1-ethyl alcohol, 2-amino-1-ethyl alcohol, and 2-ethylamino-1-ethyl alcohol.

3. In admixture, a urine sample selected for potentiometric assay, and a diluent for said sample, said diluent comprising an aqueous solution having a pH of at least about 10.0 and a predetermined concentration of a salt having the structural formula

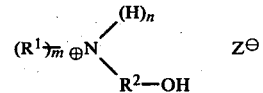

wherein $R^1$ is alkyl of from 1 to 5 carbon atoms,
$R^2$ is alkylene of from 1 to 5 carbon atoms, the oxygen-to-carbon bond of the hydroxy being no more than two bonds removed from the nitrogen,
m is 0, 1 or 2;
n is (3-m);
and Z is an acid anion,
said predetermined concentration being effective to produce a total ionic strength of said admixture within the range of about 150 millimolar and about 250 millimolar.

4. An admixture as defined in claim 3, wherein said salt is the acetate salt of an alcohol selected from the group consisting of 2-(diethylamino)-1-ethyl alcohol, 2-amino-1-ethyl alcohol, and 2-ethylamino-1-ethyl alcohol.

5. An admixture as defined in claim 1 or 3, comprising a polymer present in amounts sufficient to provide to said solution a viscosity between 1.3 centipoise and 1.9 centipoise when measured at 25° C.

6. An admixture as defined in claim 1 or 3, comprising a complexing agent for Ca⊕⊕ and Mg⊕⊕.

7. A diluent for compressing the ionic strength range of an aqueous sample, comprising an aqueous solution having
    (i) a pH of at least about 10.0;
    (ii) a predetermined concentration of
        (a) a protonated water-soluble organic amine having (i) a pKa greater than or equal to about 9.3, and (ii) a hydroxyalkyl of 1 to 5 carbon atoms, bonded to the nitrogen of the amine, wherein the oxygen-to-carbon bond of the hydroxy is no more than two bonds removed from the nitrogen and
(b) an acid anion;
said predetermined concentration being effective to produce, when 4 parts of said solution are added to 1 part of two different saline solutions, one having a total ionic strength of 130 millimolar and the other a total ionic strength of 410 millimolar, a range of said ionic strength for the diluted saline solutions that is between about 150 millimolar and about 250 millimolar; and
(iii) a polymer present in amounts sufficient to provide to said solution a viscosity between about 1.3 centipoise and about 1.9 centipoise when measured at 25° C.

8. A diluent as defined in claim 7, wherein said amine is selected from the group consisting of 2-(diethylamino)-1-ethyl alcohol, 2-amino-1-ethyl alcohol, and 2-ethylamino-1-ethyl alcohol.

9. A diluent for compressing the ionic strength of an aqueous sample, comprising an aqueous solution having
(i) a pH of at least about 10.0;
(ii) a predetermined concentration of a salt having the structural formula

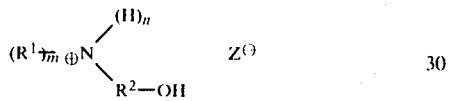

wherein
$R^1$ is alkyl of from 1 to 5 carbon atoms,
$R^2$ is alkylene of from 1 to 5 carbon atoms, the oxygen-to-carbon bond of the hydroxy being no more than two bonds removed from the nitrogen,
m is 0, 1 or 2;
n is (3-m);
and Z is an acid anion,
said predetermined concentration being effective to produce, when 4 parts of said solution are added to 1 part of two different saline solutions, one having a total ionic strength of 130 millimolar and the other a total ionic strength of 410 millimolar, a range of said ionic strength for the diluted saline solutions that is between about 150 millimolar and about 250 millimolar; and
(iii) a polymer present in amounts sufficient to provide to said solution a viscosity between about 1.3 centipoise and about 1.9 centipoise when measured at 25° C.

10. A diluent as defined in claim 9, wherein said salt is the acetate salt of an alcohol selected from the group consisting of 2-(diethylamino)-1-ethyl alcohol, 2-amino-1-ethyl alcohol, and 2-ethylamino-1-ethyl alcohol.

11. An admixture of a diluent as defined in claim 7 or 9 and a urine sample selected from potentiometric assay.

12. A diluent for compressing the ionic strength range of an aqueous sample, comprising an aqueous solution having
(i) a pH of at least about 10.0;
(ii) a predetermined concentration of
(a) a protonated water-soluble organic amine having a pKa greater than or equal to about 9.3, and a hydroxyalkyl of 1 to 5 carbon atoms, bonded to the nitrogen of the amine, wherein the oxygen-to-carbon bond of the hydroxy is no more than two bonds removed from the nitrogen, and
(b) an acid anion,
said predetermined concentration being effective to product, when 4 parts of said solution are added to 1 part of two different saline solutions, one having a total ionic strength of 130 millimolar and the other a total ionic strength of 410 millimolar, a range of said ionic strength for the diluted saline solutions that is between about 150 millimolar and about 250 millimolar; and
(ii) a complexing agent for $Ca^{\oplus\oplus}$ and $Mg^{\oplus\oplus}$.

13. A method for potentiometrically determining the concentration of an ionic analyte in an aqueous solution, comprising the steps of
(i) admixing with said solution, a predetermined concentration of
(a) a protonated water-soluble organic amine having (i) a pKa greater than or equal to about 9.3, and (ii) a hydroxyalkyl of 1 to 5 carbon atoms, bonded to the nitrogen of the amine, wherein the oxygen-to-carbon bond of the hydroxy is no more than two bonds removed from the nitrogen and
(b) an acid anion, in an amount effective to provide a pH of at least about 10.0,
(ii) contacting a quantity of the admixture with a first electrode selective for said ionic analyte,
(iii) before, during, or after step (ii), contacting a quantity of a reference liquid having a known concentration of said analyte, with a second electrode, and
(iv) allowing said quantities to make ion contact with each other to permit a detection of electrical imbalance between them.

14. A diluent for compressing the ionic strength of an aqueous sample, comprising an aqueous solution having
(i) a pH of at least about 10.0;
(ii) a predetermined concentration of a salt having the structural formula

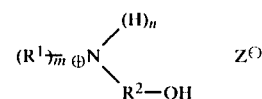

wherein
$R^1$ is alkyl of from 1 to 5 carbon atoms,
$R^2$ is alkylene of from 1 to 5 carbon atoms, the oxygen-to-carbon bond of the hydroxy being no more than two bonds removed from the nitrogen,
m is 0, 1 or 2;
n is (3-m);
and Z is an acid anion,
said predetermined concentration being effective to produce, when 4 parts of said solution are added to 1 part of two different saline solutions, one having a total ionic strength of 130 millimolar and the other a total ionic strength of 410 millimolar, a range of said ionic strength for the diluted saline solutions that is between about 150 millimolar and about 250 millimolar, and
(iii) a complexing agent for $Ca^{\oplus\oplus}$ and $Ma^{\oplus\oplus}$.

* * * * *

UNITED STATES PATENT AND TRADEMARK OFFICE
CERTIFICATE OF CORRECTION

PATENT NO. : 4,416,735
DATED : November 22, 1983
INVENTOR(S) : Thomas R. Kissel

It is certified that error appears in the above-identified patent and that said Letters Patent are hereby corrected as shown below:

Col. 5, line 46, "procedure" should read --procedures--.

Col. 6, line 2, "electrode" should read --electrodes--.

Col. 7, line 51, "involves" should read --involved--.

Col. 10, line 6, "product" should read --produce--; line 13, "(ii)" should read --(iii)--.

Signed and Sealed this

Twenty-sixth Day of February 1985

[SEAL]

*Attest:*

DONALD J. QUIGG

*Attesting Officer*   *Acting Commissioner of Patents and Trademarks*